(12) United States Patent
Polychronakos et al.

(10) Patent No.: US 6,534,272 B2
(45) Date of Patent: Mar. 18, 2003

(54) DNA ASSAY FOR THE PREDICTION OF AUTOIMMUNE DIABETES

(75) Inventors: Constantin Polychronakos, Côte St-Luc (CA); Petros Vafiadis, Laval (CA); Rosemarie Grabs, Longueuil (CA); Houria Ounissi-Benkalha, St-Laurent (CA)

(73) Assignee: McGill University, Montréal (CA)

( * ) Notice: Subject to any disclaimer, the term of this patent is extended or adjusted under 35 U.S.C. 154(b) by 0 days.

(21) Appl. No.: 09/909,962

(22) Filed: Jul. 23, 2001

(65) Prior Publication Data

US 2002/0160376 A1 Oct. 31, 2002

Related U.S. Application Data

(63) Continuation-in-part of application No. 09/389,556, filed on Sep. 3, 1999, now abandoned.

(51) Int. Cl.[7] .................. C12Q 1/68; C12P 19/34; C07H 21/04; C07K 1/00; C07K 14/00
(52) U.S. Cl. .................. 435/6; 435/91.1; 435/91.2; 530/350; 536/22.1
(58) Field of Search .................. 435/6, 91.2, 91.1; 530/350

(56) References Cited

U.S. PATENT DOCUMENTS 5,972,603 A * 10/1999 Bedford et al.
6,200,782 B1 * 3/2001 Smith

OTHER PUBLICATIONS

Vafiadis, Petros, et al., Insulin expression in human thymus is modulated by INS VNTR alleles at the IDDM2 locus, Nature Genetics, vol. 15, Mar. 1997, pp. 289–292.*

* cited by examiner

Primary Examiner—W. Gary Jones
Assistant Examiner—Arun Kr. Chakrabarti
(74) Attorney, Agent, or Firm—Ogilvy Renault; France Côté

(57) ABSTRACT

The present invention relates to a novel DNA assay for the diagnosis and/or prediction of autoimmune diabetes. The present invention relates to a DNA assay for the prediction of autoimmune diabetes in human subjects, which comprises the steps of a) obtaining a DNA sample from the subject and amplifying at least one class III allele of variable number of tandem repeats (VNTR) located upstream of the insulin gene (INS) which is associated with silencing of thymic insulin mRNA expression; and b) subjecting the sample to electrophoresis to identify the silencing class III allele.

5 Claims, 6 Drawing Sheets

S1
ACAGGGGTCCTGGGG ACAGGGGTCCGGGG ACAGGGTCCTGGGG
ACAGGGGTGTGGGG ACAGGGGTCTGGGG ACAGGGGTGTGGGG
ACAGGGGTGTGGGG ACAGGGGTCTGGGG ACAGGGGTGTGGGG
ACAGGGGTCCGGGG ACAGGGGTGTGGGG ACAGGGGTCTGGGG
ACAGGGGTGTGGGG ACAGGGGTGTGGGG ACAGGGGTCTGGGG
ACAGGGGTGTGGGG ACAGGGGTCCTGGGG ACAGGGGTGTGGGG
ACAGGGGTGTGGGG ACAGGGGTGTGGGG ACAGGGGTGTGGGG
ACAGGGGTCCTGGGG ACAGGGGTGTGGGG ACAGGGGTCCTGGGG
ACAGGGGTGTGGGG ACAGGGGTGTGGGG ACAGGGGTGTGGGG
ATAGGGGTGTGGGG ACAGGGGTGTGGGG ACAGGGGTCCTGGGG
ACAGGGGTCCTGGGG ACAGGGGTGTGGGG ACAGGGGTGTGGGG
ACAGGGGTCCTGGGG ACAGGGGTGTGGGG ACAGGGGTGTGGGG
ACAGGGGTGTGGGG ACAGGGGTGTGGGG ACAGGGGTGTGGGG
ACAGGGGTCCGGGG ACAGGGGTGTGGGG ACAGGGGTCTGGGG
ACAGGGGTGTGGGG ACAGGGGTCCTGGGG ACAGGGGTGTGGGG
ACAGGGCGTGGGG ATAGGGGTGTGGGG ACAGGGGTGTGGGG
ACAGGGGTCTGGGG ACAGGGGTGTGGGG ACAGGGGTCCGGGG
ACAGGGGTGTGGGG ACAGGGGTCTGGGG ACAGGGGTGTGGGG
ACAGGGGTGTGGGG ACAGGGGTGTGGGG ACAGGGGTCCTGGGG
ACAGGGGTGTGGGG ACAGGGGTGTGGGG

ACAGGGGTGTGGGG ACAGGGGTCTGGGG ACAGGGGTGTGGGG
ACAGGGGTCCGGGG ACAGGGGTGTGGGG ACAGGGGTCTGGGG
ACAGGGGTGTGGGG ACAGGGGTCTGGGG ACAGGAGTGTGGGG
ACAGGGGTGTGGGG ACAGGGGTGTGGGG ACAGGGGTGTGGGG
ACAGGGGTCCTGGGG ACAGGGGTGTGGGG ACAGGGGTGTGGGG
ACAGGGGTCCTGGGG ACAGGGGTGTGGGG ACAGGGGTGTGGGG
ACAGGGGTGTGGGG ACAGGGGTCCGGGG ACAGGGGTGTGGGG
ACAGGGGTGTGGGG ACAGGGGTGTGGGG ACAGGGGTGTGGGG
ACAGGGGTCCGGGG ACAGGGGTGTGGGG ACAGGGGTCTGGGG
ACAGGGGTGTGGGG ACAGGGGTGTGGGG ACAGGGGTCTGGGG
ACAGGGGTGTGGGG ACAGGGGTGTGGGG ACAGGGGTGTGGGG
ACAGGGGTCTGGGG ACAGGGGTGTGGGG ACAGGGGTGTGGGG
ACAGGGGTGTGGGG ACAGGGGTCCTGGGG ACAGGGGTGTGGGG
ACAGGGGTCTGGGG ACAGGGGTGTGGGG ATAGGGGTGTGGGG
ACAGGGGTGTGGGG ACAGGGGTCCTGGGG ACAGGGGTCTGGGG
ACAGGGGTGTGGGG ATAGGGGTGTGGGG ACAGGGGTGTGGGG
ACAGGGGTGTGGGG ACAGGGGTCCTGGGG ACAGGGGTCTGGGG
ACAGGGGTGTGGGG ATAGGGGTGTGGGG ACAGGGGTGTGGGG
ACAGGGGTGTGGGG ACAGGGGTGTGGGG ACAGGGGTCCTGGGG
ACAGGGGTCTGGGG ACAGGGGTGTGGGG

ACAGGGGTGTGGGG ACAGGGGTGTGGGG ACAGGGGTGTGGGG
ACAGGGGTCCTGGGG ACAGGGGTGTGGGG ACAGGGGTGTGGGG
ACAGGGGTGTGGGG ACAGGGGTGTGGGG ATAGGGGTGTGGGG
ACAGGGGTGTGGGG ACAGGGGTGTGGGG ACAGGGGTCCTGGGG
ACAGGGGTGTGGGG ACAGGGGTGTGGGG ACAGGGGTCCTGGGG
ACAGGGGTGTGGGG ACAGGGGTGTGGGG ACAGGGGTCCCGGGG
ACAGGGGTGTGGGG ACAGGGGTGTGGGG ACAGGGGTGTGGGG
ACAGGGGTGTSGGG ACAGGGGTCCCGGGG ACAGGGGTGTGGGG
ACAGGGGTGTGGGG ACAGGGGTCCTGGGG ACAGGGGTCTGAGG
ACAGGGGTGTGGGC ACAGGGGTCCTGGGG ACAGGGGTCCTGGGG
ACAGGGGTCCTGGGG ACAGGGGTCTGGGG

FIG. 2A

E1
```
ACAGGGGTCCTGGGG ACAGGGGTCCGGGG ACAGGGTCCTGGGG
ACAGGGGTGTGGGG ACAGGGGTCTGGGG ACAGGGGTGTGGGG
ACAGGGGTGTGGGG ACAGGGGTCTGGGG ACAGGGGTGTGGGG
ACAGGGGTCCGGGGG ACAGGGGTGTGGGG ACAGGGGTCTGGGG
ACAGGGGTGTGGGG ACAGGGGTGTGGGG ACAGGGGTCTGGGG
ACAGGGGTGTGGGG ACAGGGGTCCTGGGG ACAGGGGTGTGGGG
ACAGGGGTGTGGGG ACAGGGGTGTGGGG ACAGGGGTGTGGGG
ACAGGGGTCCTGGGG ACAGGGGTGTGGGG ACGGGGGTCCTGGGG
ACAGGGGTGTGGGG ACAGGGGTGTGGGG ACAGGGGTGTGGGG
ATAGGGGTCTGGGG ACAGGGGTGTGGGG ACAGGGGTCCTGGGG
ACAGGGGTCCTGGGG ACAGGGGTGTGGGG ACAGGGGTGTGGGG
ACAGGGGTCCTGGGG ACAGGGGTGTGGGG ACAGGGGTGTGGGG
ACAGGGGTGTGGGG ACAGGGGTGTGGGG ACAGGGGTGTGGGG
ACAGGGGTCCGGGGG ACAGGGGTGTGGGG ACAGGGGTCTGGGG
ACAGGGGTGTGGGG ACAGGGGTCCTGGGG ACAGGGGTGTGGGG
ACAGGGGTGTGGGG ATAGGGGTGTGGGG ACAGGGGTGTGGGG
ACAGGGGTCTGGGG ACAGGGGTGTGGGG ACAGGGGTCCGGGGG
ACAGGGGTGTGGGG ACAGGGGTCTGGGG ACAGGGGTGTGGGG
ACAGGGGTGTGGGG ACAGGGGTGTGGGG ACAGGGGTCCTGGGG
ACAGGGGTGTGGGG ACAGGGGTGTGGGG

ACAGGGGTGTGGGG ACAGGGGTCTGGGG ACAGGGGTGTGGGG
ACAGGGGTCCGGGGG ACAGGGGTGTGGGG ACAGGGGTCTGGGG
ACAGGGGTGTGGGG ACAGGGGTCTGGGG ACAGGGGTGTGGGG
ACAGGGGTGTGGGG ACAGGGGTGTGGGG ACAGGGGTGTGGGG
ACAGGGGTCCTGGGG ACAGGGGTGTGGGG ACAGGGGTGTGGGG
ACAGGGGTCCTGGGG ACAGGGGTGTGGGG ACAGGGGTGTGGGG
ACAGGGGTGTGGGG ACAGGGGTCCGGGGG ACAGGGGTGTGGGG
ACAGGGGTGTGGGG ACAGGGGTGTGGGG ACAGGGGTGTGGGG
ACAGGGGTCCGGGGG ACAGGGGTGTGGGG ACAGGGGTCTGGGG
ACAGGGGTGTGGGG ACAGGGGTGTGGGG ACAGGGGTCTGGGG
ACAGGGGTGTGGGG ACAGGGGTGTGGGG ACAGGGGTGTGGGG
ACAGGGGTCTGGGG ACAGGGGTGTGGGG ACAGGGGTGTGGGG
ACAGGGGTGTGGGG ACAGGGGTCCTGGGG ACAGGGGTGTGGGG
ACAGGGGTCTGGGG ACAGGGGTGTGGGG ATAGGGGTGTGGGG
ACAGGGGTGTGGGG ACAGGGGTCCTGGGG ACAGGGGTCTGGGG
ACAGGGGTGTGGGG ATAGGGGTGTGGGG ACAGGGGTGTGGGG
ACAGGGGTGTGGGG ACAGGGGTCCTGGGG ACAGGGGTCTGGGG
ACAGGGGTGTGGGG ATAGGGGTGTGGGG ACAGGGGTGTGGGG
ACAGGGGTGTGGGG ACAGGGGTGTGGGG ACAGGGGTCCTGGGG
ACAGGGGTCTGGGG ACAGGGGTGTGGGG

ACAGGGGTGTGGGG ACAGGGGTGTGGGG ACAGGGGTGTGGGG
ACAGGGGTCCTGGGG ACAGGGGTGTGGGG ACAGGGGTGTGGGG
ACAGGGGTGTGGGG ACAGGGGTGTGGGG ATAGGGGTGTGGGG
ACAGGGGTGTGGGG ACAGGGGTGTGGGG ACAGGGGTCCTGGGG
ACAGGGGTGTGGGG ACAGGGGTGTGGGG ACAGGGGTCCTGGGG
ACAGGGGTGTGGGG ACAGGGGTGTGGGG ACAGGGGTCCCGGGG
ACAGGGGTGTeGGG ACAGGGGTGTGGGG ACAGGGGTGTGGGG
ACAGGGGTGTGGGG ACAGGGGTCCCGGGG ACAGGGGTGTGGGG
ACAGGGGTGTGGGG ACAGGGGTCCTGGGG ACAGGGGTCTGAGG
ACAGGGGTGTGGGC ACAGGGGTCCTGGGG ACAGGGGTCCTGGGG
ACAGGGGTCCTGGGG ACAGGGGTCTGGGG
```

FIG. 2B

S1    cniabaabakabaabacaaaacacaaaeaccaacaaaaakabacaqeabakabaaacaa
E1    cniabaabakabaabacaaaacaoaaapaccaacaaaaakabacaaeabakabaaacaa S1    abakababraaacaacaaakaaaakabaabaaabaaacabaeacbaeaacbaeaaacba
E1    abakababaaaacaacaaakaaaakabaabaaabaaacabaeacbaeaacbaeaaacba S1    aaacaaaaeaacaacaadaaaadaacghcccb
E1    aaacaaaaeaacaacaadaaaadaacghcccb

FIG. 2C

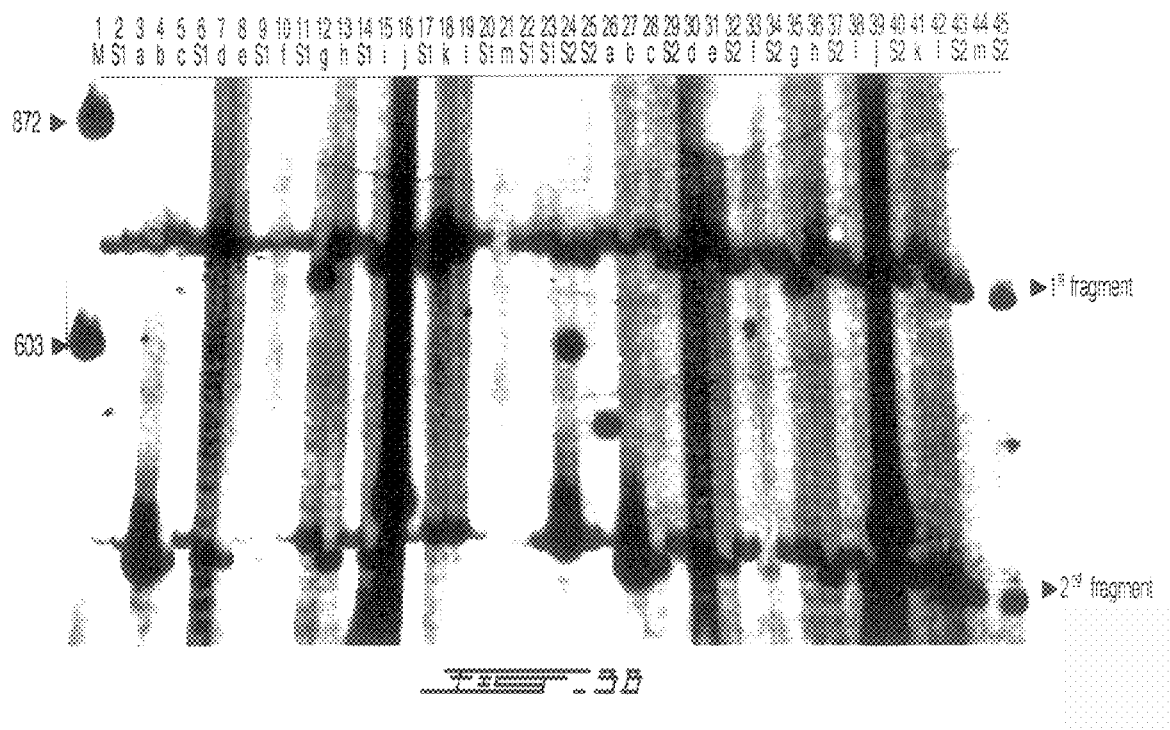

DNA ASSAY FOR THE PREDICTION OF AUTOIMMUNE DIABETES

This application is a continuation-in-part of U.S. application Ser. No. 09/389,556 filed Sep. 3, 1999 and claiming priority from Canadian patent application 2,246,487 filed Sep. 3, 1998.

BACKGROUND OF THE INVENTION (a) Field of the Invention

The invention relates to a novel DNA assay for the diagnosis and/or prediction of autoimmune diabetes.

(b) Description of Prior Art

Diabetes is a major cause of morbidity and mortality in industrialized societies. It has been estimated that one of every seven health-care dollars goes to treating diabetes and its complications. Type 1 diabetes (also called insulin-dependent or juvenile diabetes, henceforth referred to in this document as "diabetes") is due to the autoimmune destruction of the insulin-producing pancreatic β-cells. Type 1 diabetes is less common than type 2, accounting for only 10–20% of cases in Caucasians. However, because it is much more severe and starts much earlier in life, it accounts for a large proportion of diabetes-related morbidity and mortality.

Type 1 diabetes involves autoimmune destruction of the insulin-producing pancreatic β-cells. Insulin, an autoantigen in this process, is expressed in human thymus at levels dependent on alleles at the upstream INS VNTR, to which the IDDM2 susceptibility locus has been mapped. Chromosomes carrying the dominantly protective (Bennett S T et al., 1995, Nat. Genet. 9(3):284–292), long INS VNTR alleles (class III) produce 2–3 times higher levels of insulin gene (INS) mRNA than those with predisposing, short class I alleles (Vafiadis P et al., 1997, Nat Genet. 15(3):289–292; Pugliese A et al., 1997, Nat. Genet. 15(3):293–297).

Prevention of Diabetes

It is estimated that by the time symptoms of diabetes appear, more than 95% of the β-cell mass has been destroyed. Given the irreversibility of this destruction, the most promising approach to the disease is prevention. This will require an intervention, at some time before symptoms appear, aimed at modulating the immune system to prevent the antigen-specific autoimmune reaction. Although the specific causative autoantigen(s) in diabetes is (are) not known, insulin, the main product of the β-cell, appears to be an autoantigen of major importance.

Based on this, the DPT (diabetes prevention trial) a large study, is now underway in the United States. Oral insulin administration is used in the hope of helping individuals at risk for diabetes acquire immune tolerance to insulin. The results of this study will not be known for a number of years. It is possible that it will be superseded by other studies, which will be based on more precise scientific rationale provided by current spectacular advances in immunology. There is a tangible likelihood that in the coming decade a safe and effective method of preventing or reversing the diabetes autoimmune process will have been found.

Identification of Individuals at Risk

An effective intervention to prevent diabetes is very unlikely to be inexpensive, safe and convenient enough to be applied to the general population (i.e. in the fashion of infectious disease vaccines). The intervention will most likely need to be targeted to individuals that can be identified as being at a substantial risk for diabetes.

Autoantibody Testing

The DPT and similar trials have focused on first-degree relatives of diabetics that are positive for autoantibodies known to predict diabetes. These autoantibodies against protein components of the β-cell become positive at least a year or two before the onset of clinical diabetes. However, even if diabetes is prevented with 100% efficacy in all first-degree relatives of diabetics, this will only abolish less than 10% of new cases of diabetes, as the majority of individuals with diabetes do not have a previously affected first-degree relative. To be meaningful, an effective prevention will have to be applicable to the general population. Screening the general population for antibodies has been shown to be feasible in practice, and predictive of diabetes. However, since antibodies only become positive at a finite time point before the onset of diabetes, most people destined to become diabetic at some future point will be negative when tested early in life. Therefore, antibody screening of the general population will need to be repeated at intervals of 1–2 years, a totally impractical proposition.

Genetic Testing

An alternative way of predicting high risk for diabetes is through DNA testing. It is known that genetic predisposition plays a major role in diabetes. Identical twins of individuals with diabetes have a risk that ranges from 30 to >60% in various studies, as opposed to fraternal twins, that are concordant only in 5–10% of the cases (Bennett S T et al., 1996, Ann. Rev. Genet. 30:343–370). The predisposition is not inherited in a Mendelian fashion, which means that this complex phenotype requires predisposing genetic material involving more than a single gene. Linkage studies have identified as many as 18 different genetic loci that are potentially linked to diabetes (in genetics, the term "locus" is used instead of "gene", when only a location in the genome is known, but the gene[s] involved remain[s] to be identified). Although many of these loci will probably turn out to be statistical artifacts, it is clear that in order to define the "diabetes genotype", markers at more than one loci will have to be typed. A good definition of the "diabetes genotype" would be: a combination of alleles that correctly predicts diabetes with a probability that approaches that predicted from being the identical twin of a diabetic. Obviously, a risk of at least 30% would justify preventive intervention.

So far only two of the several loci have been defined precisely enough to be used to this end. They are termed IDDM1 and IDDM2, and can be used already to obtain a certain degree of risk estimation (Bennett S T et al., 1996, Ann. Rev. Genet. 30:343–370). Using similar approaches several more loci can be likewise defined, that together predict diabetes with specificity that approaches that of the idealized diabetes genotype. Specificity in a diagnostic test is the percentage of positive tests that turn out to be true. The twin studies show that 30–60% is the best specificity that can be achieved with DNA testing, but even a specificity of 10% or less can be very useful depending on how safe, simple and inexpensive future preventive interventions turn out to be.

Once defined, the loci could be genotyped on a few drops of blood obtained at birth as part of neonatal screening programs currently in place for other diseases. Those individuals who exceed a certain threshold of risk can then be followed with antibody testing or treated prior to the appearance of autoantibodies, depending on what the optimal strategy will be determined to be.

Conventional Testing at the IDDM2 locus

It involves determination of the VNTR by Southern blotting, a cumbersome technique that is not easily amenable to miniaturization and automation (Bennett S T et al., 1995, *Nat. Genet.* 9(3):284–292). Polymerase chain reaction (PCR) has been used to identify class I alleles, but there is no published report of successful amplification of class III alleles.

More importantly, the conventional Southern blotting approach only allows classification of individuals as having no class III allele (genotype: I/I) or having at least one class III allele (genotype I/III or III/III). Individuals in the latter category will be assigned a risk that is approximately 4-fold less (Bennett S T et al., 1996, *Ann. Rev. Genet.* 30:343–370), and this estimate will be entered in a formula along with information from other IDDM loci, in order to calculate risk. The risk assignment can be erroneous in individuals carrying the specific alleles S1 or S2.

Given the foregoing, it would be desirable to develop a novel DNA assay for the diagnosis and/or prediction of autoimmune diabetes which overcomes the drawbacks of the prior art. More particularly, an assay by which alleles predisposing for diabetes could be distinguished from protective alleles would be desirable.

SUMMARY OF THE INVENTION

One aim of the present invention is to provide a PCR-based method to distinguish not only between class I and class III alleles of the insulin VNTR, but also between different alleles within class III.

Accordingly, in one aspect, the present invention provides a DNA assay for the prediction of autoimmune diabetes in a human subject where predisposition to autoimmune diabetes in a human subject is indicated by the presence of at least one Class III allele of the INS VNTR which silences thymic insulin expression, said assay comprising the steps of:

a) obtaining a DNA sample from the subject and subjecting the sample to PCR amplification using a primer pair specific for class III alleles of the INS VNTR;

b) subjecting the amplified sample to digestion with a restriction enzyme having a cleavage site on an uncommon variant of the repeat unit of the Class III allele; and c) subjecting the digested sample to electrophoresis to identify the presence of a class III allele which silences thymic insulin expression.

Specifically, the method of the present invention can reliably distinguish alleles in class III that silence thymic insulin expression from those that enhance thymic insulin expression. This distinction is very important, as the present genetic studies show that such "silencing" class III alleles are predisposing to diabetes, while most class III alleles are protective. As used herein, the phrase "silence thymic insulin expression" refers to the lack of insulin mRNA expression in the thymus of individuals possessing certain class III alleles.

Commercial Applications of the DNA Assay

The DNA assay of the present invention can be easily adapted to a miniaturized, automated genotyping approach utilizing fluorescent labeling. This genotyping will be an important part of a panel of genotypes that will determine diabetes risk.

Advantages and Improvements over Existing Technology

The assay of the present invention is PCR-based, which makes it ideal for miniaturization and automation. The applicants are the first to develop a protocol for the successful amplification of class III insulin VNTR, technically a challenging task, as it involves amplification of highly repetitive GC-rich fragments of 2–3 kb length, well beyond the sizes handled by conventional PCR.

It distinguishes "silencing" class III alleles, such as the S1 and S2 alleles (described in greater detail herein), from other class III alleles, and assigns a higher rather than a lower risk to them, which will improve both the sensitivity and the specificity of the method. This is the main advantage of the assay of the present invention over the prior art.

To illustrate the importance of the assay of the present invention, the following must be considered:

The applicants have examined 167 diabetic children. Of these, 16 had a paternally transmitted S1 or S2 allele (high-risk class III). The conventional method, unable to distinguish S1 and S2 alleles, would have assigned to them the four-fold lower risk associated with class III as a whole. The assay of the present invention assigns them the true risk conferred by these alleles, which is 4.6-fold higher.

Thus, 16 of 167 children, almost 10%, would have been erroneously given a risk sixteen-fold lower than appropriate. Ten per cent of the population may not seem to be much, but it must be born in mind that in a complex disease like diabetes, a universal risk determination must be pieced together from evaluation of small effects at each locus. For this reason, the assay of the present invention is very likely to become an indispensable part of any attempt to predict diabetes.

In a preferred embodiment of the present invention, the DNA assay is employed to identify S1 and S2 class III alleles of the insulin VNTR whereby identification of an S1 or S2 allele is indicative of at least 1% risk of autoimmune diabetes, which is >10 fold higher than that erroneously predicted by existing methods of the prior art.

The INS VNTR is composed of a variable number of tandem 14–15 bp repeat sequences, with the consensus repeat unit ACA GGGG TGT GGGG (SEQ ID NO:1).

The amplification of step a) is effected using at least one primer pair selected from the group consisting of VNTR5 (TCAGGCTGGACCT CCAGGTGCCTGTTCTG) (SEQ ID NO:2)/VNTR6 (GCTGGTCCTGAGGM GAGGTGCTGACGA) (SEQ ID NO:3) and VNTR7 (GGCATCTTGGGCC ATCCGGGACTG) (SEQ ID NO:4)/ VNTR8 (GCAGGGCGGGGCTCTTTGCGCTG) (SEQ ID NO:5).

The sample is selected from the group consisting of blood, saliva, urine and hair follicle.

The electrophoretic co-migration of step b) is effected using PAGE.

In another aspect of the present invention, isolated Class III alleles of the INS VNTR associated with silencing of thymic insulin mRNA expression are provided, including for example, S1 and S2 alleles.

In a further aspect of the present invention, primer pairs for PCR amplification of class III alleles of variable number of tandem repeats (VNTR) located upstream of the insulin gene (INS) are provided comprising: VNTR5 (TCAGGCTGGACCTCCAGGTGCCTGTTCTG) (SEQ ID NO:2)/VNTR6(GCT GGTCCTGAGGAAG AGGTGCTG ACGA) (SEQ ID NO:3) and VNTR7 (GGCATCT

TGGGCCATCCGGGACTG) (SEQ ID NO:4) VNTR8 (GCAGGGCGGGGCTCTTT GCGCTG) (SEQ ID NO:5).

BRIEF DESCRIPTION OF THE DRAWINGS

FIGS. 2A and 2B illustrates the DNA sequences of the cloned S1 and E1 class III alleles (SEQ ID Nos: 6 & 7), respectively;

FIG. 2C illustrates the same sequences in a different notation wherein each individual repeat is represented by a letter, as previously described (Bennett S T et al., 1996, Ann. Rev. Genet. 30:343–370)

DETAILED DESCRIPTION OF THE INVENTION

Figure 1:
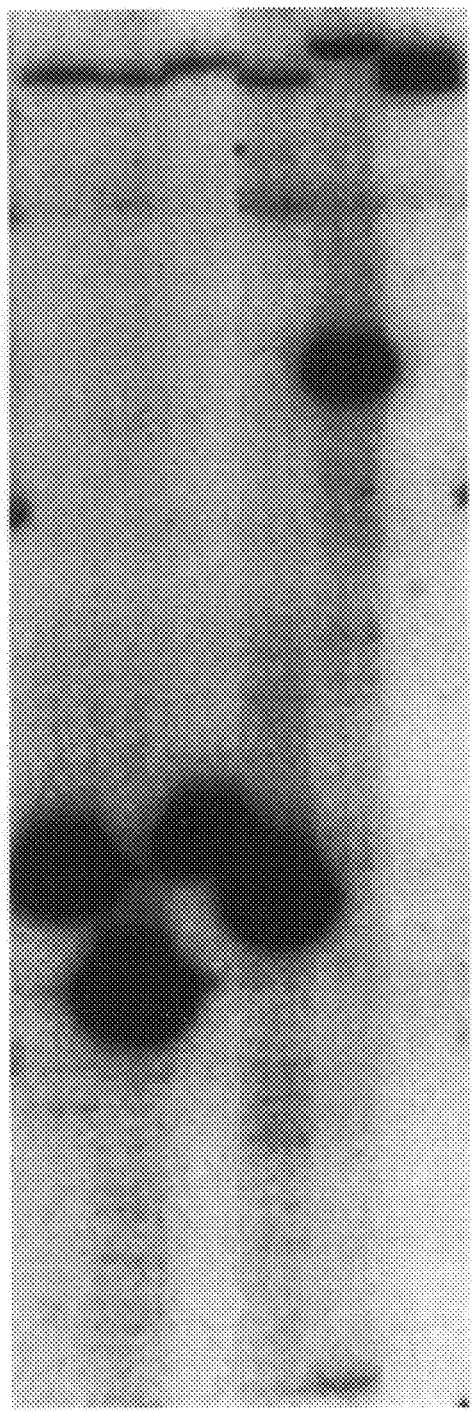
FIG. 1 illustrates the amplification products of the INS VNTR PCR protocol for all classes are shown for samples with monoallelic (m) or biallelic (b) INS expression in thymus.

Type 1 diabetes involves autoimmune destruction of the insulin-producing pancreatic β-cells. Insulin, an autoantigen in this process, is expressed in human thymus at levels dependent on alleles at the upstream INS VNTR, to which the IDDM2 susceptibility locus has been mapped (Bennett S T et al., 1995, Nat Genet. 9(3):284–292; Bennett S T et al., 1996, Ann. Rev. Genet. 30:343–370). Chromosomes carrying the dominantly protective, long INS VNTR alleles (class III) produce 2–3 times higher levels of insulin gene (INS) mRNA than those with predisposing, short class I alleles (Vafiadis P et al., 1997, Nat. Genet. 15(3):289–292; Pugliese A et al., 1997, Nat. Genet. 15(3):293–297). Higher thymic INS expression may promote better induction of immune tolerance to βcells. However, a few specific class III INS VNTR alleles are associated with complete silencing of thymic INS expression (Vafiadis P et al., 1997, Nat Genet. 15(3):289–292; Pugliese A et al., 1997, Nat. Genet. 15(3):293–297). Our hypothesis predicts that such alleles are predisposing rather than protective. To test this prediction, we examined the distortion of transmission of two such silencing alleles (S1 and S2) from non-diabetic parents to 167 diabetic children, using a novel PCR-based method of restriction fingerprinting. Transmission of S1+S2 from heterozygous parents was significantly less frequent than expected, while all other class III alleles (i.e. non-S1 and non-S2) showed a significant undertransmission as expected.

Early reports suggested the presence on an insulin-like factor in the thymus. The applicants and others demonstrated that the insulin gene (INS) was transcribed and translated in human fetal (Vafiadis P et al., 1997, Nat Genet. 15(3):289–292) and postnatal thymus (Pugliese A et al., 1997, Nat. Genet. 15(3):293–297). In the majority of thymus samples selected to be INS VNTR class I/III heterozygotes, thymic INS expression was 2–3 times higher from the gene copy linked to the class III allele as compared to the class I allele. In 5 of 22 samples, however, INS expression was completely silenced from the copy linked to the class III allele, while the class I linked copy was expressed. Monoallelic expression has been observed in genes subject to genomic imprinting, which involves silencing of either the paternal or the maternal allele. We showed that the difference in thymic INS expression levels between class I and III alleles is independent of parental origin, thus ruling out partial imprinting as the cause of this difference (Vafiadis P et al., 1997, Nat. Genet. 15(3):289–292). However, parental DNA corresponding to the thymus samples with "silencing" class III alleles was not available, so it could not be determined whether genomic imprinting may explain this observation.

Insulin is the only known β-cell specific type 1 diabetes autoantigen. An autoimmune reaction against INS-encoded epitopes may thus result in specific targeting of the pancreatic β-cells for destruction, and increased thymic INS expression could explain the dominantly protective effect of class III alleles through better tolerance induction, a thymic process that is known to be dose-dependent.

If the above hypothesis that thymic INS expression has a dose-dependent effect on susceptibility to type 1 diabetes is correct, then alleles associated with silencing of thymic INS expression would be more predisposing than all other alleles. To test this hypothesis, we have compared the transmission frequency of class III alleles matching two class III alleles associated with silencing of INS expression (which we call S1 and S2) to all other alleles, from heterozygous parents to diabetic offspring. We predicted that silencing-associated class III alleles of the S1 and S2 type would be transmitted to diabetic offspring more often than other alleles. Furthermore, we predicted that if silencing of thymic INS expression is due to genomic imprinting, the transmission distortion of S1 and S2 type class III alleles would be confined to transmissions from only one parental sex. Thus, silencing of INS in the thymus would be due to allele-specific genomic imprinting, similar to what we have described for the human IGF2R gene.

The Known Diabetes Susceptibility Loci

IDDM1

This is the major diabetes locus, accounting for almost half of the genetic component. It is located on chromosome 6p21, and involves the cluster of class II HLA histocompatibility genes. PCR-based testing exists to identify several alleles, some of which are predisposing to diabetes while others are protective or neutral. Individuals with the protective alleles are extremely unlikely to have the disease, but the predisposing alleles are common in the general population, and the specificity of predicting diabetes based on their presence is low. Additional loci must be determined for meaningful prediction.

IDDM2

This locus has been mapped to chromosome 11 p15.5, to a polymorphism consisting of variable number of tandem repeats (VNTR), 0.5 kb upstream of the insulin gene (INS). The number of repeats in each of the two copies of an individual's chromosome 11 can range from 40 to several hundred. Short VNTR alleles (40–60 repeats) are the most common and are classified together as class I. Long alleles (>120 repeats) are called class III and are found in about 20% of Caucasian chromosomes, while intermediate class II alleles (60–120 repeats) are extremely rare. Individuals who have inherited a chromosome with a class III allele from at least one parent have a 3–5 fold less probability of diabetes than those who have a class I allele on both chromosomes. Therefore, class III alleles, as a group, can be considered dominantly protective.

Recently, we demonstrated a putative mechanism for the protective effect of the class III VNTR: We found that the human thymus produces small amounts of insulin, and chromosomes with a class III allele make 2–3 times more insulin mRNA in the thymus than those with class I.

However, in a small number of cases the class III chromosome instead of producing more than the class I, produced no insulin at all! We predicted that those specific class III alleles associated with this paradoxical phenomenon (called S alleles, for "silencing") will not be protective (as expected of class III alleles) but must be predisposing. Indeed studies on 167 diabetic children and their parents confirmed that, although class III alleles as a whole were inherited less often than expected by chance alone, the S alleles were actually transmitted much more often.

To test our hypothesis, we first developed a PCR based method of identifying INS VNTR alleles. The INS VNTR is composed of a variable number of tandem 14–15 bp repeat sequences, with the consensus repeat unit ACA GGGG TGT GGGG (Bennett S T et al., 1996, Ann. Rev. Genet. 30:343–370). In Caucasians, most alleles are either in the class I (26–63 repeats) or the longer class III (140–210 repeats) category (Bennett S T et al., 1996, Ann. Rev. Genet. 30:343–370). Initially, these alleles were studied by Southern blot, and later the class I alleles were studied by PCR (Bennett S T et al., 1995, Nat. Genet. 9(3):284–292; Bennett S T et al., 1996, Ann. Rev. Genet. 30:343–370). Due to the high GC-rich content and repetitive nature of this sequence, resulting in a highly stable intramolecularly folded structure, amplification of the long class III alleles has not been possible by PCR. Here, we present the first report, to our knowledge, of PCR amplification for all classes of INS VNTR alleles, including class III and the intermediate-sized class II alleles, by a single PCR protocol (FIG. 1). The first four samples have a class I/III genotype, the next has a class I/II genotype, and the final sample has two class III alleles distinguishable by size. The number of repeat units in each class I allele is shown. Co-dominant segregation of class III alleles within families confirmed the high fidelity of the method and the stability of these alleles within families. This technique represents an important advancement in the study of the IDDM2 susceptibility locus.

We used this technique to clone the class III allele from one of our two informative thymus samples with complete silencing of INS expression from the class III chromosome (allele S1) (Vafiadis P et al., 1997, Nat. Genet. 15(3):289–292). The identity and integrity of the cloned allele, S1 was repeatedly demonstrated by showing electrophoretic co-migration of PCR amplification products from both genomic and cloned DNA templates (n>15). This indicates that the two products are the same size, and thus no major recombinational event resulting in loss of sequence has occurred in the cloned allele. Similarly, both cloned and genomic DNA demonstrated the same RFLP band pattern after Msp1 digestion (Msp1 recognizes an uncommon variant of the repeat unit (Bennett S T et al., 1996, Ann. Rev. Genet. 30:343–370)), suggesting the same arrangement of internal repeat sequences. In fact, any restriction enzyme recognizing an uncommon variant of the repeat unit could be used. Hpa2 is an example of another useful restriction enzyme. To further verify the identity of the S1 clone, the clone was sequenced (FIG. 2A). Using the same methods, we similarly cloned and confirmed a class III allele (E1) associated with enhanced expression of thymic INS as compared to a class I allele (FIG. 2B) and defined three sequence differences between them, likely responsible for the differential transcriptional effect.

To test our hypothesis regarding the mechanism of IDDM2 encoded susceptibility, 167 families consisting of mother, father and type 1 diabetes affected child were genotyped for the INS VNTR by this PCR method. In Caucasians, about 75% of INS VNTR alleles are class I and about 25% are class III alleles. The parental genotypes in our mostly Caucasian population follow this distribution with 59% class I/I, 37% I/III and 4% III/III as compared to expected frequencies of 56% I/I, 38% I/III and 6% III/III. As expected, the genotype frequencies in affected offspring were skewed towards a higher percentage of predisposing class I/I genotypes: 68% I/I, 28% I/III and 4% III/III. From this group, 139 parental class III alleles could be unambiguously determined to have been transmitted or not-transmitted to diabetic offspring from mothers or fathers. We used cloned and genomic DNA to PCR amplify the S1 allele. Similarly, we used genomic DNA to amplify the class III allele associated with silencing of thymic INS expression in a second sample (which we call S2) and S2-identical alleles (see Methods). These were then used as markers against which all parental class III alleles were compared and identified as S1 or S2 type alleles or as non-S1/non-S2 type alleles.

Each allele was determined to either be the same size or a different size than alleles S1 or S2 by PAGE on a long gel (38.5 cm). All class III alleles analyzed were either larger than both S1 and S2, smaller than S1 and S2 or equal in size to either S1 or S2 (FIG. 3).

Figure 3A:
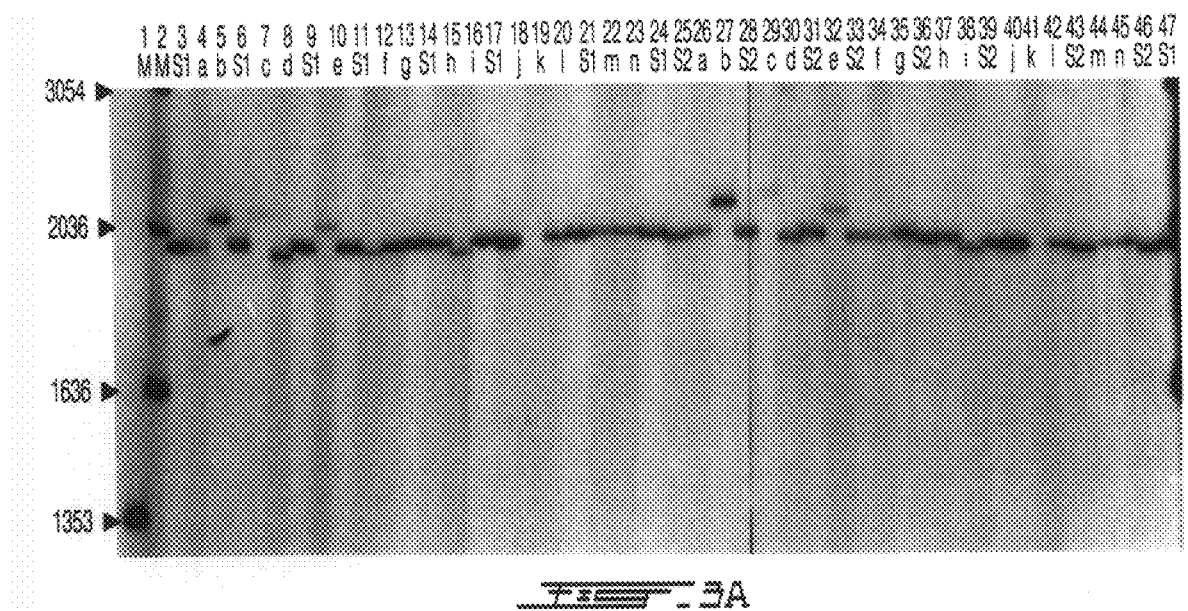
FIG. 3 illustrates the identification of class III alleles as S1 or S2 type.

The class III INS VNTR alleles in families with a type 1 diabetes offspring (a to n) are compared in terms of size to the class III alleles associated with silencing of thymic INS expression (S1 and S2) (FIG. 3A). These include father-affected offspring (b & c) and mother-affected offspring (m & n) pairs. The class III INS VNTR alleles in families with a type 1 diabetes offspring (a to m, not the same samples as in A) are compared in terms of Msp1 RFLP to the class III alleles associated with silencing of thymic INS expression (S1 and S2) (FIG. 3B). These include a mother-affected offspring pair (a & b). The size in bp of molecular weight standards are shown at the left.

Thus, the S1 allele is only slightly larger than the S2 allele, and there are no allele sizes between them that can be resolved by our method. Furthermore, each class III allele was loaded into two separate wells of the polyacrylamide gel for comparison to S1 and S2 separately. Those that were equal in size to S1 were always larger than the S2 allele, and those that were equal in size to S2 were always smaller than S1 allele. This indicates that the same alleles behave in a consistent manner between separate loadings in PAGE and that our method can consistently identify small differences in migration distance.

In addition to size, we attempted to distinguish alleles by repeat unit composition through comparison of their Msp1 RFLP band pattern (fingerprint). Class III alleles were classified as either the same as or different from S1 or S2 (FIG. 3). Most alleles had two large digestion fragments that were well above the largest digestion fragments from any of the class I alleles. Thus for class 1/111 heterozygotes, we were able to distinguish between class I and III digestion fragments in this size range (see Methods). The size of the largest digestion fragment did not vary much between alleles. Similarly, the second largest fragments from most alleles were all within a narrow size range. This indicates that most class III alleles have a very similar sequence composition. The exception to this were the class III alleles present in an uncommon haplotype, previously referred to as the very protective haplotype (VPH) (Bennett S T et al., 1995, Nat. Genet. 9(3):284–292), which were much more thoroughly digested than those from the common protective haplotypes (PH) (Bennett S T et al., 1995, *Nat. Genet.* 9(3):284–292), resulting in much smaller digestion fragments. Thus, class III alleles found in the VPH are smaller and likely contain more copies of the repeat sequence recognized by Msp1 than the more common class III alleles found in the PH. The size and Msp1 analyses were also combined such that class III alleles were considered as S1 or S2 type alleles only if they matched the S1 or S2 allele, respectively, in terms of size and Msp1 RFLP pattern. Alleles were thus designated as S1 or S2 type alleles based on size only, Msp1 RFLP only, or based on both size and Msp1 RFLP.

Preliminary analysis of transmission disequilibrium in the first 167 samples is summarized in tables 1–3. Table 1 shows transmission of alleles determined to be non-S1 and non S2 from non-diabetic parents to diabetic children. As expected, they are undertransmitted because of their dominant protective effect, and there is no significant transmission distortion between maternal and paternal alleles (Table 1).

TABLE 1

Transmission analysis of non-S1 and non-S2 class III alleles

| Alleles | Transmitted | Not transmitted | p-value $X^2$ test |
|---|---|---|---|
| By size only: | | | |
| Maternal non-S1 or non-S2 | 14 | 22 | 0.96 |
| Paternal non-S1 or non-S2 | 18 | 26 | |
| By Mspl RFLP only: | | | |
| Maternal non-S1 or non-S2 | 18 | 40 | 0.23 |
| Paternal non-S1 or non-S2 | 24 | 31 | |
| By size and Mspl RFLP: | | | |
| Maternal non-S1 or non-S2 | 21 | 43 | 0.27 |
| Paternal non-S1 or non-S2 | 26 | 33 | |

Tables 2 and 3 summarize transmissions of paternal or maternal S1+S2 alleles, compared to all other non-S1, non-S2 alleles. Alleles that are identical to S1 or S2 by both size and Msp1 RLFP are overtransmitted in contrast to non-S alleles that are undertransmitted, but because of the small numbers the difference is not statistically significant.

TABLE 2

Transmission analysis of maternal S1 and S2 class III alleles

| Alleles | Transmitted | Not transmitted | p-value $X^2$ test |
|---|---|---|---|
| By size only: | | | |
| Maternal S1 or S2 | 10 | 24 | 0.38 |
| Maternal and Paternal non-S1 or non-S2 | 32 | 48 | |
| By Mspl RFLP only: | | | |
| Maternal S1 or S2 | 7 | 6 | 0.38 |
| Maternal and Paternal non-S1 or non-S2 | 42 | 71 | |
| By size and Mspl RFLP: | | | |
| Maternal S1 or S2 | 5 | 3 | 0.32 |
| Maternal and Paternal non-S1 or non-S2 | 47 | 76 | |

TABLE 3

Transmission analysis paternal S1 and S2 class III alleles

| Alleles | Transmitted | Not transmitted | p-value $X^2$ test |
|---|---|---|---|
| By size only: | | | |
| Not-paternal S1 or S2 | 42 | 72 | 0.023 |
| Paternal S1 or S2 | 16 | 9 | |
| By Mspl RFLP only: | | | |
| Not-paternal S1 or S2 | 49 | 77 | 0.06 |
| Paternal S1 or S2 | 9 | 4 | |
| By size and Mspl RFLP: | | | |
| Not-paternal S1 or S2 | 52 | 79 | 0.11 |
| Paternal S1 or S2 | 6 | 2 | |

The results became statistically significant when results from the 120 diabetic children in the 60 sibling pairs from the Human Biological Data Interchange were added to the analysis. This analysis is summarized in Table 4.

TABLE 4

Summary of transmissions from nondiabetic parents to a diabetic child

| | | Transmission involving | |
|---|---|---|---|
| | Total transmissions | S1 or S2 | All other Class III |
| Untransmitted | | 6 | 99 |
| Transmitted | | 12 | 62 |
| Total | 1148 | 18 | 161 |
| | | P = 0.025 | |

We examined 287 diabetic children and 227 pairs of parents (908 parental chromosomes). In the 60 HBDI families that had two children transmissions were calculated twice, once for each child. Therefore, the total number of transmissions was higher than the number of parental chromosomes.

The results of the transmission analysis as summarized in Table 4 are as follows. Non-S class III alleles were transmitted at a frequency significantly less than 0.5, as expected from the known dominant protective effect of class III as a whole. As our hypothesis had predicted, S alleles behaved as predisposing rather than protective: they were much more frequently transmitted than all other class III alleles (P=0.025 by Fisher's exact test). Because in most cases the transmitting parent's other allele was a class I, S-type alleles seem to behave as more predisposing than even class I alleles, as our hypothesis would predict based on thymic insulin expression levels.

In order to ascertain if all S1 and S2 type alleles, as determined by the above methods, are associated with silencing of thymic INS expression, we characterized the class III alleles in 16 class I/III samples which express both INS copies in the thymus. Most of the class III alleles (15/16) were different from S1 or S2 alleles by size and/or Msp1 RFLP analysis, while one was found to be identical to S1 by size and Msp1 RFLP pattern. Despite this, it is associated with enhanced thymic INS expression relative to the class I allele. There may two likely explanations for this. First, since parental origin in this sample was unknown, the class III allele could be of maternal origin, and therefore not expected to silence thymic INS expression. Alternatively, it could be a paternal allele that is different from S1 and S2 in terms of small differences in size and/or sequence variation not differentiated by Msp1 digestion. Note that the E1 allele which we have cloned is from this individual, thus E1 is an S1-type allele by size and Msp1 analysis, although it behaves like most class III alleles as an enhancer of INS expression in thymus relative to class I alleles.

We have undertaken an analysis of the INS VNTR role in type 1 diabetes. The results of this study provide further evidence that IDDM2 contributes to the pathogenesis of type 1 diabetes through an immunoregulatory mechanism. The INS VNTR may affect the level of thymic INS expression and thus the efficiency of immune tolerance induction to this -cell restricted autoantigen. This may have important implications for clinical trials of insulin prophylaxis in type 1

Methods

DNA Samples

DNA was extracted using a phenol-chloroform method from 167 blood samples collected from patients of the Montreal Children's Hospital diabetes clinic and their parents, and from participants of the Minneapolis branch of the multicenter study of the natural history of diabetic nephropathy in type 1 diabetes. Samples were obtained with signed, informed consent and approval by the Institutional Review Board of the Maisonneuve-Rosemont Hospital. In addition, we examined 120 DNA samples from 60 diabetic sibling pairs from the Human Biological Data Interchange (HBDI). DNA from both parents was available in all cases. All patients developed insulin-dependent diabetes under the age of 19, except for two HBDI patients who were 29 and 34 at onset but were included because the other sibling in the pair had young onset.

Human fetal thymus tissues were obtained at the time of pregnancy termination with written consent from the mother. The tissue was pulverized under liquid nitrogen and DNA and RNA were extracted using phenol-chloroform under neutral and acid conditions, respectively.

INS VNTR PCR For All Classes

The PCR reaction for amplification of all classes of INS VNTR alleles contained approximately 100–200 ng genomic DNA or 0.0000235 ng of Pvull digested cloned DNA, 0.2 mM of each dNTP, 1 $\mu$Ci P32-dCTP, 1 mM MgCl2, 2.5 $\mu$l 10×NH4 PCR Reaction buffer (ID Labs), 0.375 units ID-Zyme thermostable DNA polymerase (ID Labs), 100 ng of sense primer and 100 ng of antisense primer. The primers used were either VNTR5 (TCAGGCTGGA CCTCCAGGTGCCTGTTCTG) (SEQ ID NO:2) and VNTR6 (GCTGGTCCTGAGG AAGAGGTGCTGACGA) (SEQ ID NO:3) previously described by Bennett et al (Vafiadis P et al., 1997, *Nat. Genet.* 15(3):289–292) or the newly designed VNTR7 (GGCATCTTGGGCCAT CCGGGACTG) (SEQ ID NO:4) and VNTR8 (GCAGGGCGGGGCTCUTTGCGCTG) (SEQ ID NO:5) primers that directly flank the INS VNTR and are present in the cloned DNA. The PCR was carried out for 25–26 cycles of: 94° C./30 sec denaturation, 62° C./30 sec annealing and 70° C./3 min 30 sec plus a 4 sec extension per cycle. Products were visualized by polyacrylamide gel electrophoresis (PAGE) and autoradiography.

Cloning of INS VNTR Alleles

The INS VNTR alleles to be cloned were PCR amplified using the VNTR5 and VNTR6 primers. The PCR product was double digested with NcoI (recognizes a site 33 bp 5' to the INS VNTR), and PstI (recognizes a site 28 bp 3' to the INS VNTR). The NcoI/PstI double digestion product was desalted with the Wizard DNA Clean-up System (Promega Corp.), concentrated by evaporation and purified from a low melting agarose gel following electrophoresis using the Wizard PCR Preps DNA Purification System (Promega Corp.) Similarly, the Promega T vector was digested in the polylinker region with NcoI and PstI, dephosphorylated with CIAP (Gibco-BRL), and purified from a low melting agarose gel using the Wizard PCR Preps DNA Purification System (Promega Corp.). The INS VNTR allele was then directionally ligated into the T-vector using T4 DNA Ligase (Gibco-BRL). The ligation reaction was transformed into JM109 competent cells (Promega Corp.) and clones containing the INS VNTR-T vector construct were identified by restriction analysis.

DNA Sequencing of Cloned INS VNTR Alleles

The highly repetitive nature of the VNTR precludes the use of restriction subcloning or internal primers for sequencing. Therefore, the S1 allele and a class III allele associated with enhanced thymic insulin expression (E1), were sequenced by generating a series of overlapping unidirectional deletions from a NcoI-PstI fragment subcloned into a pGEM-T vector using the Exo-Size deletion kit (New England Biolabs Inc., Beverly, Mass.). Exonuclease III digestion of the construct linearized by double digestion with SphI and NcoI, both on the 5' end of the insert shortens the insert but not the vector, which is protected by the 3' overhang left by SphI.

Identification of Class III Alleles as S1 or S2 Type Alleles

To determine if particular class III alleles were the same size as either the S1 or S2 allele, they were amplified by PCR using the VNTR7/VNTR8 primer pair and electrophoresed on a 38.5 cm long 8% polyacrylamide gel for approximately 6 hours at 60 watts. To distinguish small differences in size, PCR product from the S1 and S2 alleles were loaded in every 2 to 4 lanes, interspersed throughout the alleles whose size was to be determined. The migration distance of the unknown allele was then compared to the adjacent S1 or S2 allele. The S1 allele was amplified from cloned and/or genomic DNA, and the migration distance of the unknown alleles were compared to that of the S1 allele. Almost every gel had at least one PCR product (many had several) amplified from S1 genomic DNA loaded in a well next to PCR product from cloned DNA. In all cases, the PCR product from cloned S1 and genomic S1 DNA migrated to the exact same distance, indicating that PCR product from the cloned S1 allele DNA template is identical to the genomic DNA template. Similarly, the S2 allele was amplified from genomic DNA and compared in size to other class III alleles. As this allele was not cloned and genomic DNA quantities of the S2 allele were limited, an allele found to be identical in size to S2 was used as a size marker for the S2 allele. PCR product from this marker allele was electrophoresed with PCR product from genomic DNA containing the S2 allele, and in all cases they migrated to the same distance, indicating that they are the same size by our method. Furthermore, most gels had multiple loadings of PCR product from the S1 allele genomic DNA next to the marker S1 allele and again, they migrated to the same distance in all cases. Thus, PCR product of class III alleles was loaded onto a polyacrylamide gel, adjacent to PCR product from S1 or S2 alleles, electrophoresed and determined to be either the same size or a different size than S1 and S2 alleles.

The same PCR products were digested with Msp1 and electrophoresed in a 38.5 cm long 8% polyacrylamide gel for 4 hours at 60 watts. The same type of analysis and controls were used as for the size analysis described above. For most samples, the two largest Msp1 digestion fragments were compared between the unknown class III allele and the S1 and S2 alleles. In class I/III individuals, these fragments are always located above even the largest class I allele digestion fragments and are of much lower abundance due to preferential amplification of the smaller class I alleles over the class III alleles. This was determined by comparing the Msp1 digestion fragments in a number of class I/III individuals obtained from PCR product where only the class I allele is amplified (using the previously described PCR conditions (Bennett S T et al., 1995, *Nat. Genet.* 9(3) :284–292)) and PCR product from our PCR protocol for all classes which amplifies both class I and III alleles.

The present invention will be more readily understood by referring to the following examples which are given to illustrate the invention rather than to limit its scope.

EXAMPLE I

A child is screened for diabetes risk, in a future implementation of a genetic screening to identify candidates for a preventive intervention. Based on the cost, inconvenience, and risk of the intervention it has been decided that it is well worth treating five individuals exceeding the risk threshold, even though only one will develop diabetes if untreated. The threshold is therefore set to a value that requires a specificity of 20%.

The particular child tests positive for a paternally transmitted S1 allele, using the method of the present invention. The maternal allele is an ordinary class I. By existing technology, the assigned I/III genotype will be deemed to confer an approximately four-fold less risk than I/I, the most common Caucasian genotype (Bennett S T et al., 1996, *Ann. Rev. Genet.* 30:343–370). By the method of the present invention, it will be assigned a four-fold higher risk than all other IDDM2 genotypes. Thus, without the present invention, the child will have been assigned a risk estimate of an order of magnitude lower than the correct value. No matter what the genotype in other loci is, this error is likely to result in misclassification of most individuals in this situation.

Based on the frequency of the untransmitted alleles (Tables 2 and 3) this misclassification will apply to 7% of all individuals in a population screen.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A DNA assay for the prediction of autoimmune diabetes in human subjects where predisposition, to autoimmune diabetes in a human subject is indicated by the presence of at least one Class III allele of the INS VNTR of a subtype that silences thymic insulin expression, said assay comprising the steps of:
   a) obtaining a DNA sample from the subject and subjecting the sample to PCR amplification using a primer pair specific for said class III allele;
   b) subjecting the amplified sample to digestion with a restriction enzyme having a cleavage site on an uncommon variant of the repeat unit of the class III allele; and
   c) subjecting the digested sample to electrophoresis to test for the presence of a fragment pattern identical to that of specific class III allele subtypes demonstrated to predispose to autoimmune diabetes which silences thymic insulin expression, wherein said class III allele of the INS VNTR is S1 allele having a DNA sequence as set forth in SEQ ID No: 6.

2. The DNA assay of claim 1, wherein the PCR amplification step is conducted using the ID-zyme thermostable DNA polymerase.

3. A DNA assay for the prediction of autoimmune diabetes in human subjects where predisposition to autoimmune diabetes in a human subject is indicated by the presence of at least one Class III allele of the INS VNTR of a subtype that silences thymic insulin expression, said assay comprising the steps of:
   a) obtaining a DNA sample from the subject and subjecting the sample to PCR amplification using a primer pair specific for said class III allele;
   b) subjecting the amplified sample to digestion with a restriction enzyme having a cleavage site on an uncommon variant of the repeat unit of the class III allele; and
   c) subjecting the digested sample to electrophoresis to test for the presence of a fragment pattern identical to that of specific class III allele subtypes demonstrated to predispose to autoimmune diabetes which silences thymic insulin expression,
wherein the PCR amplification step is effected using at least one primer pair selected from the group consisting of VNTR5 (TCAGGCTGGACCTCCAGGTGCCTGTTCTG) (SEQ ID NO:2)/VNTR6 (GCTGGT CCTG AGGAAGAGGTGCTGACGA) (SEQ ID NO:3) and VNTR7 (GGCATCT TGGGCCATCCGGGACTG) (SEQ ID NO: 4)/VNTR8 (GCAGGGCGGGGCTCT TTGCGCTG) (SEQ ID NO: 5).

4. The DNA assay of claim 1, wherein the restriction enzyme recognizes the cleavage site CCGG.

5. The DNA assay of claim 4, wherein the restriction enzyme is Msp1 or Hpa2.

* * * * *

SEQUENCE LISTING

<160> NUMBER OF SEQ ID NOS: 7

<210> SEQ ID NO 1
<211> LENGTH: 13
<212> TYPE: DNA
<213> ORGANISM: Artificial Sequence
<220> FEATURE:
<223> OTHER INFORMATION: consensus repeat unit

<400> SEQUENCE: 1 acagggtgt ggg                                                        13

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
tcaggctgga cctccaggtg cctgttctg                                      29

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gctggtcctg aggaagaggt gctgacga                                       28

<210> SEQ ID NO 4
<211> LENGTH: 24
<212> TYPE: DNA
<213> ORGANISM: Artificial Sequence
<220> FEATURE:

```
<223> OTHER INFORMATION: primer

<400> SEQUENCE: 4
ggcatcttgg gccatccggg actg                                              24

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gcagggcggg gctctttgcg ctg                                               23

<210> SEQ ID NO 6
<211> LENGTH: 2130
<212> TYPE: DNA
<213> ORGANISM: human

<400> SEQUENCE: 6 acagggtcc  tggggacagg  ggtccgggga  cagggtcctg  ggacagggg   tgtggggaca    60 gggtctggg  gacagggtg   tggggacagg  ggtgtgggga  cagggtctg   ggacagggg    120 tgtggggaca gggtccgggg  ggacagggt   gtggggacag  gggtctgggg  acagggtgt    180 ggggacaggg gtgtggggac  agggtctgg   ggacagggt   gtggggacag  ggtcctggg    240 gacagggtg  tggggacagg  ggtgtgggga  cagggtgtg   gggacagggg  tgtggggaca    300 gggtcctgg  ggacagggt   gtggggacag  gggtcctggg  gacagggtg   tggggacagg    360 ggtgtgggga cagggggtgtg  gggatagggg  tgtgggggaca ggggtgtggg gacagggtc    420 ctggggacag gggtcctggg gacagggtg   tggggacagg   ggtgtgggga  cagggtcct    480 ggggacaggg gtgtggggac  agggtgtgg   ggacagggt   gtggggacag  gggtgtgggg    540 acagggtgt  ggggacaggg  gtccgggga   cagggtgtg   ggacagggg   tctggggaca    600 ggggtgtggg gacagggtc   ctggggacag  gggtgtgggg  acagggcgt   gggatagggg    660 gtgtggggac agggtgtgg   ggacagggt   ctggggacag  gggtgtgggg  acagggtcc    720 gggggacagg ggtgtgggga  cagggtctg   ggacagggg   tgtggggaca  gggggtgtggg    780 gacagggtg  tggggacagg  ggtcctgggg  acagggtgt   ggggacaggg  gtgtggggac    840 agggtgtgg  ggacagggt   ctggggacag  gggtgtgggg  acagggtcc   ggggacagg    900 ggtgtgggga cagggtctg   ggacagggg   tgtggggaca  gggtctggg   gacaggagtg    960 tggggacagg ggtgtgggga  cagggtgtg   ggacagggg   tgtggggaca  gggtcctgg    1020 ggacagggt  gtggggacag  gggtgtgggg  acagggtcc   tggggacagg  ggtgtgggga    1080 cagggtgtg  ggacagggg   tgtggggaca  gggtccggg   ggacagggt   gtggggacag    1140 gggtgtgggg acagggtgt   ggggacaggg  gtgtgggac   agggtccgg   gggacagggg    1200 tgtggggaca gggtctggg   gacagggtg   tggggacagg  ggtgtgggga  cagggtctg    1260 ggacagggg  tgtggggaca  gggtgtggg   gacagggtg   tggggacagg  ggtctgggga    1320 cagggtgtg  ggacagggg   tgtggggaca  gggtgtggg   gacagggtc   ctggggacag    1380 gggtgtgggg acagggtct   ggggacaggg  gtgtggggat  aggggtgtgg  ggacagggt    1440 gtggggacag gggtcctggg  gacagggtc   tggggacagg  ggtgtgggga  taggggtgtg    1500
gggacagggg tgtggggaca  ggggtgtggg  gacagggtc   ctggggacag  gggtctgggg    1560 acagggtgt  ggggatagg   gtgtgggga   cagggtgtgg  ggacagggt   gtggggacag    1620
```

-continued

| | |
|---|---|
| gggtgtgggg acaggggtcc tggggacagg ggtctgggga caggggtgtg gggacagggg | 1680 |
| tgtggggaca ggggtgtggg gacaggggtg tggggacagg ggtcctgggg acagggtgt | 1740 |
| ggggacaggg gtgtggggac aggggtgtgg ggacaggggt gtgggatag gggtgtgggg | 1800 |
| acagggtgt ggggacaggg gtgtggggac agggtcctg ggacaggggt gtggggaca | 1860 |
| ggggtgtggg gacaggggtc tggggacag ggtgtgggg acagggtgt ggggacaggg | 1920 |
| gtcccgggga caggggtgtg gggacaggggt gtggggaca ggggtgtggg gacaggggtg | 1980 |
| tggggacagg ggtcccgggg acaggggtgt ggggacaggg gtgtgggac aggggtcctg | 2040 |
| gggacagggg tctgaggaca ggggtgtggg cacaggggtc ctggggacag ggtcctggg | 2100 |
| gacagggtc ctggggacag ggtctgggg | 2130 |

<210> SEQ ID NO 7
<211> LENGTH: 2130
<212> TYPE: DNA
<213> ORGANISM: human

<400> SEQUENCE: 7

| | |
|---|---|
| acagggtcc tggggacagg ggtccgggga caggggtcctg ggacaggggt gtggggaca | 60 |
| ggggtctggg gacagggtg tggggacagg ggtgtgggga caggggtctg ggacagggg | 120 |
| tgtggggaca ggggtccggg ggacaggggt gtggggacag ggtctgggg acagggtgt | 180 |
| ggggacaggg gtgtggggac aggggtctgg ggacagggt gtggggacag ggtcctggg | 240 |
| gacaggggtg tggggacagg ggtgtgggga caggggtgtg gggacagggg tgtggggaca | 300 |
| ggggtcctgg ggacaggggt gtggggacgg ggtcctggg gacaggggtg tggggacagg | 360 |
| ggtgtgggga caggggtgtg gggatagggg tctggggaca ggggtgtggg gacaggggtc | 420 |
| ctggggacag ggtcctggg gacaggggtg tggggacagg ggtgtgggga caggggtcct | 480 |
| ggggacaggg gtgtggggac aggggtgtgg ggacaggggt gtggggacag gggtgtgggg | 540 |
| acagggtgt ggggacaggg gtccgggga caggggtgtg ggacaggggt ctggggaca | 600 |
| ggggtgtggg gacaggggtc ctggggacag ggtgtgggga caggggtgt ggggatagggg | 660 |
| gtgtgggac agggtgtgg ggacaggggt ctggggacag ggtgtgggga caggggtcc | 720 |
| ggggggacagg ggtgtgggga caggggtctg ggacaggggt gtggggaca ggggtgtggg | 780 |
| gacaggggtg tggggacagg ggtcctgggg acaggggtgt ggggacaggg gtgtggggac | 840 |
| aggggtgtgg ggacaggggt ctggggacag ggtgtgggga caggggtcc ggggggacagg | 900 |
| ggtgtgggga caggggtctg ggacagggg tgtggggaca ggggtctggg gacaggggtg | 960 |
| tggggacagg ggtgtgggga caggggtgtg gggacaggggt gtggggaca ggggtcctgg | 1020 |
| ggacaggggt gtggggacag ggtgtgggg acagggtcc tggggacagg ggtgtgggga | 1080 |
| caggggtgtg gggacagggg tgtggggaca ggggtccggg ggacaggggt gtggggacag | 1140 |
| ggtgtgggg acagggtgt ggggacagggg tgtggggac aggggtccgg gggacagggg | 1200 |
| tgtggggaca ggggtctggg gacaggggtg tggggacagg ggtgtgggga caggggtctg | 1260 |
| ggacaggggt gtggggacag gggtgtggg gacaggggtg tggggacagg ggtctgggga | 1320 |
| caggggtgtg gggacagggg tgtggggaca ggggtgtggg gacaggggtc ctggggacag | 1380 |
| ggtgtgggg acaggggtct ggggacaggg gtgtgggat aggggtgtgg ggacaggggt | 1440 |
| gtggggacag gggtcctggg gacaggggtc tggggacagg ggtgtgggga taggggtgtg | 1500 |
| ggacaggggt gtggggacag gggtgtgggg acaggggtc ctggggacag ggtctgggg | 1560 |

-continued

```
acagggtgt gggataggg gtgtggggac agggggtgtgg ggacaggggt gtggggacag    1620
gggtgtgggg acagggggtcc tggggacagg ggtctgggga cagggggtgtg gggacagggg    1680 tgtggggaca gggggtgtggg gacagggggtg tggggacagg ggtcctgggg acagggtgt    1740 ggggacaggg gtgtggggac agggggtgtgg ggacaggggt gtggggatag gggtgtgggg    1800 acagggtgt ggggacaggg gtgtggggac agggggtcctg gggacaggggg tgtggggaca    1860 gggggtgtggg gacagggggtc ctggggacag gggtgtgggg acagggtgt ggggacaggg    1920 gtcccgggga cagggggtgtg gggacagggg tgtggggaca gggggtgtggg gacagggggtg    1980 tggggacagg ggtcccgggg acagggtgt ggggacaggg gtgtggggac agggggtcctg    2040 gggacagggg tctgaggaca gggggtgtggg cacagggggtc ctggggacag gggtcctggg    2100 gacagggggtc ctggggacag gggtctgggg                                    2130
```